(12) United States Patent
Marcum

(10) Patent No.: US 6,530,659 B1
(45) Date of Patent: *Mar. 11, 2003

(54) COLLAPSIBLE EYE WEAR FEATURING FACE CONTACTING PADS

(76) Inventor: Steven R. Marcum, 912 44th St., Sacramento, CA (US) 95819

( * ) Notice: Subject to any disclaimer, the term of this patent is extended or adjusted under 35 U.S.C. 154(b) by 0 days.

This patent is subject to a terminal disclaimer.

(21) Appl. No.: 09/812,173

(22) Filed: Mar. 16, 2001

Related U.S. Application Data

(63) Continuation-in-part of application No. PCT/US99/17837, filed on Aug. 6, 1999.

(51) Int. Cl.$^7$ ................................................. G02C 1/50
(52) U.S. Cl. ............................ 351/41; 351/63; 351/156; 351/158
(58) Field of Search ............................ 351/44, 41, 156, 351/157, 110, 83, 111, 63; 2/12, 13, 245; 206/5

(56) References Cited

U.S. PATENT DOCUMENTS

| | | | |
|---|---|---|---|
| 3,419,909 A | | 1/1969 | Spain |
| 3,526,449 A | | 9/1970 | Bolle |
| 4,165,925 A | | 8/1979 | Donovan |
| 4,251,302 A | | 2/1981 | Leonard |
| 4,603,442 A | | 8/1986 | Barfield |
| 4,747,681 A | | 5/1988 | Brower |
| 4,852,185 A | | 8/1989 | Olson |
| 4,852,189 A | | 8/1989 | Duggan |
| 4,945,574 A | | 8/1990 | Dagher |
| 5,016,999 A | | 5/1991 | Williams |
| D321,703 S | | 11/1991 | Grau |
| 5,213,241 A | * | 5/1993 | Dewar et al. .................. 206/5 |
| D339,363 S | | 9/1993 | Larner |
| 5,245,709 A | | 9/1993 | Shipcott |
| 5,331,356 A | | 7/1994 | Chiou |
| 5,343,258 A | | 8/1994 | Lachman |
| 5,386,254 A | | 1/1995 | Kahaney |
| 5,412,438 A | | 5/1995 | Bolle |
| 5,581,312 A | | 12/1996 | Chen |
| 5,604,547 A | | 2/1997 | Davis |
| 5,631,717 A | | 5/1997 | Spector |
| 5,825,455 A | | 10/1998 | Fecteau |
| 5,969,786 A | * | 10/1999 | Marcum ....................... 351/63 |

FOREIGN PATENT DOCUMENTS

| | | |
|---|---|---|
| CH | 678 981 A | 11/1991 |
| DE | 93 08 554 U | 8/1993 |

OTHER PUBLICATIONS

Rollens Post–mydriatic Sunglasses; www.americanet.com/rollens/ Feb. 1, 1998.*
Rollens Professional Products; Rollens Post–Mydriatic Sunglasses; "http://www.americanet.com/Rollens/" internet website; Feb. 1, 1998; entire document.

* cited by examiner

*Primary Examiner*—Hung Xuan Dang
(74) *Attorney, Agent, or Firm*—Heisler & Associates

(57) ABSTRACT

An eye wear assembly 10 is provided which includes a film-like, resilient collapsible lens 20 that wraps about the eyes of the wearer W from temple T to temple T. The lens 20 is partially held in place by its left and right wings 30 which include respective left and right temple pads 40. The lens 20 is offset from the face of the wearer W by horizontal pads 60 which increase the wearer's W comfort and provide circulation via two primary vents 70 to allow perspiration to dissipate from the enclosure created between the lens 20 and the wearer's W face. A nose cutout region 90, conforming to the general shape of a typical user's nose N, is provided at the midpoint of the lens 20 at its bottom edge 28. A nose saddle 100, made of soft, resilient foam or rubber-type material, is attached adjacent the nose cutout region 90 on the rear concave surface 24 of the lens 20. The nose saddle 100 conforms to the shape of the nose N of the wearer W. A retention band 200 extends from the left and right edges 32 of the left and right wings 30 to provide a secure means for retaining the lens 20 on the face of the wearer W. A cylindrical container 300 provided for stowage of the eye wear assembly 10 in a rolled-up orientation is also described.

20 Claims, 5 Drawing Sheets

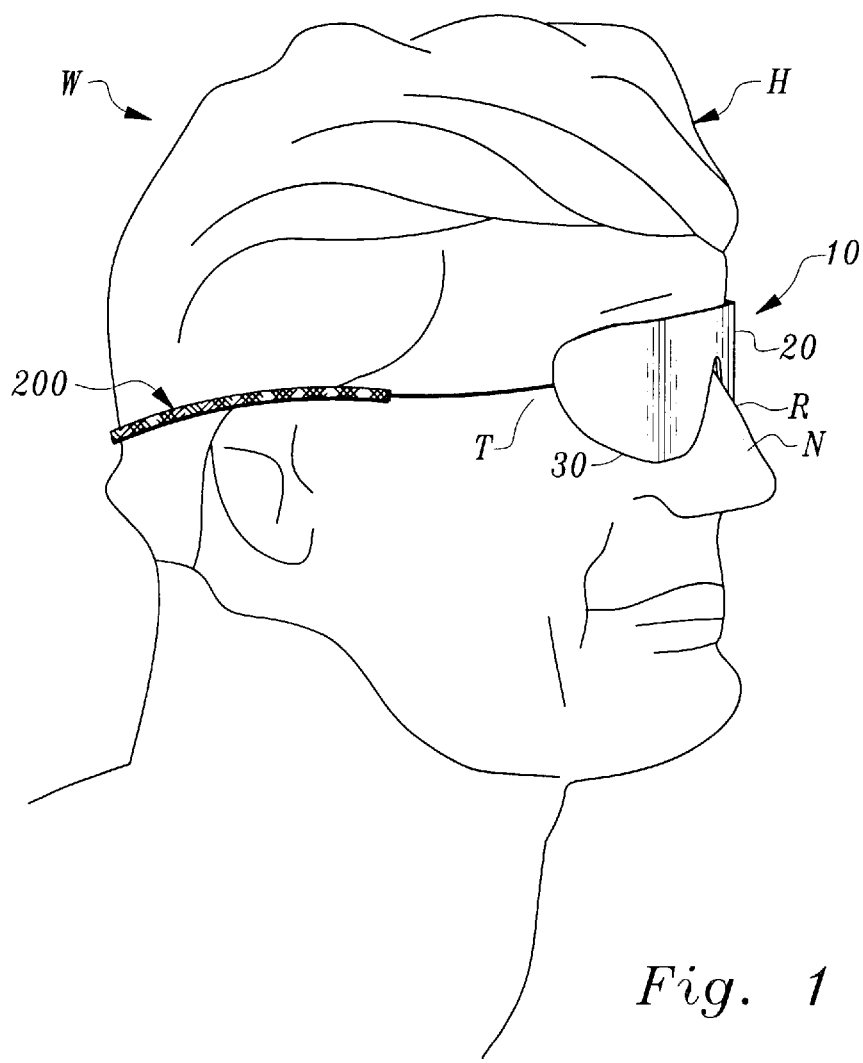
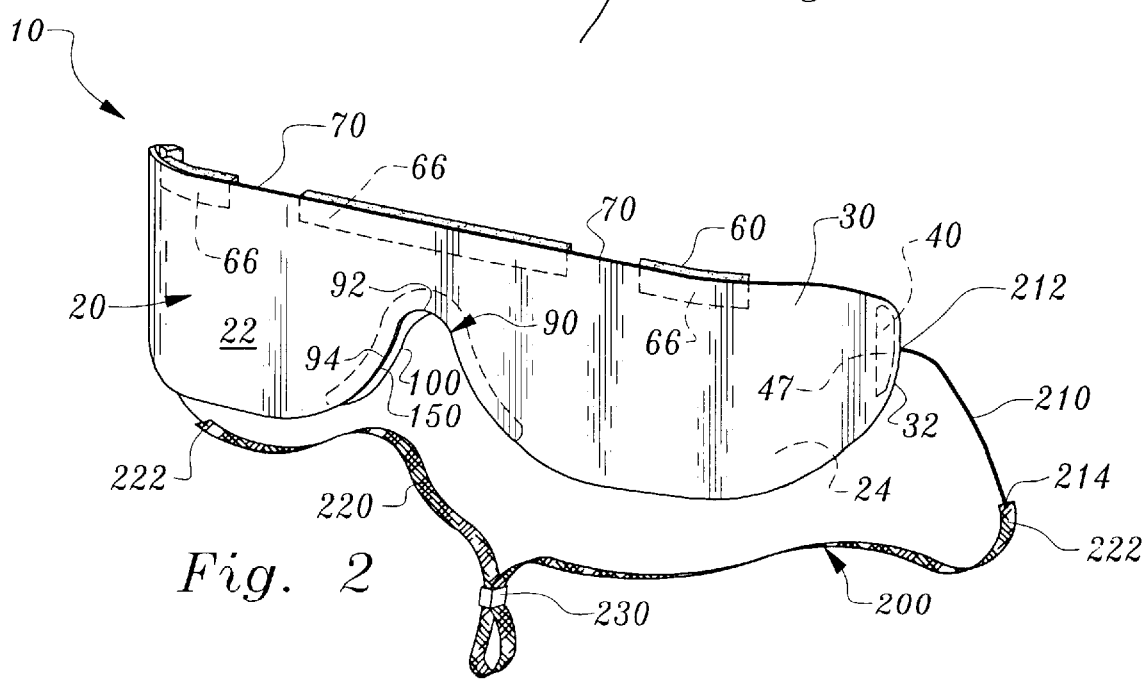

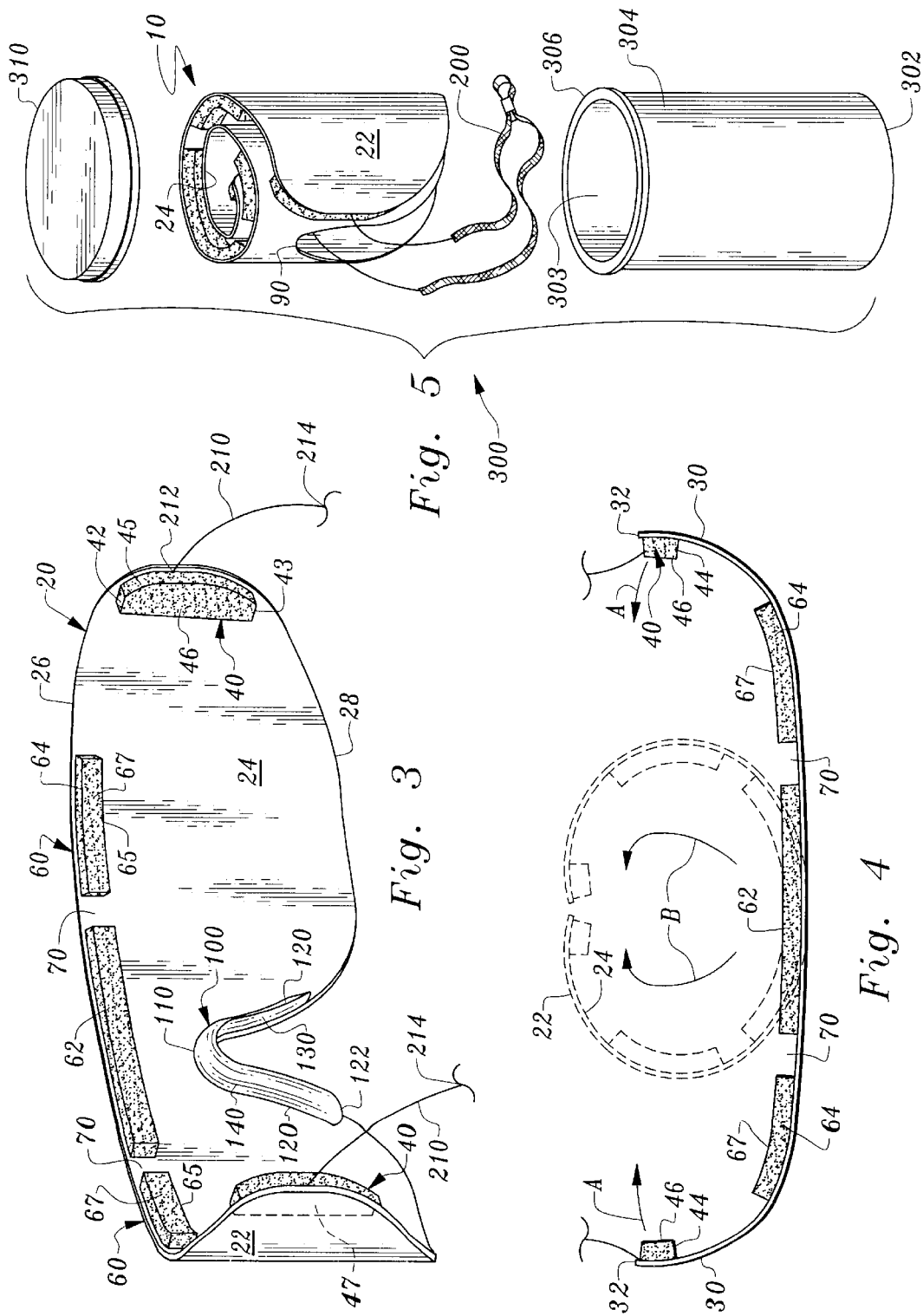

COLLAPSIBLE EYE WEAR FEATURING FACE CONTACTING PADS

CROSS-REFERENCE TO RELATED APPLICATION

This application is a continuation-in-part of Patent Cooperation Treaty International Application No. PCT/US99/17837, filed on Aug. 6, 1999.

FIELD OF THE INVENTION

The present invention relates to eye wear. More particularly, this invention relates to lightweight flexible, collapsible, portable eye wear with strategically located pads to prevent the edges of the lens of the eye wear from pinching the wearer's face, while still allowing the eye wear assembly to be easily collapsed to fit within a small portable container.

BACKGROUND OF THE INVENTION

Eye wear is available in a myriad of designs and configurations. Given the continued development of new plastics, the trend has been toward eye wear designs which are extremely lightweight, yet still robust.

One type of lightweight eye wear is used specifically for protecting the eyes of wearers after ophthalmic surgery or other types of eye treatment. These types of eye protectors are commonly known as post-mydriatic sunglasses and are designed to completely wrap around the wearer's eyes. In some cases, the wearer's eyes may be very sensitive to light due to previous pupil dilation which has not yet subsided, requiring a tinted lens. In other circumstances, e.g., cataract surgery, the eye protector needs to completely envelop the patient's eyes to ensure any potentially damaging dust or other particles are not blown into the eyes. Post-mydriatic sunglasses are also intended to prevent a patient from inadvertently rubbing the eyes, which could prove disastrous given recent delicate surgery.

Rollens Professional Products, Inc. of Denver, Colo., produces a version of post-mydriatic sunglasses which consists of a single collapsible film-like lens. In their natural relaxed state, the Rollens sunglasses tend to close into a spiral. The Rollens post-mydriatic sunglasses are designed only for use by eye patients with an immediate and reasonably short-lived need.

The Rollens lens is held in place on the wearer's face by its natural tendency to collapse to its relaxed spiral state. Clamping or gripping forces are created when the lens is unwound and placed on the face of a wearer. The tension forces cause the edges of the Rollens lens to frictionally engage the wearer's temples.

The benefits of the Rollens configuration include portability, ability to fit any size face, low cost, and the provision of a wrap-around configuration. However, the Rollens lens is known to be somewhat uncomfortable. The edges of the lens, which secure the lens to the wearer's face, tend to pinch the wearer at the temples. In addition, the placement of the non-breathable plastic lens against the wearer's skin induces perspiration. The perspiration is irritating to the wearer, and, causes the lens to more easily slip off the wearer's face by reducing the friction between the inside surface of the lens and the wearer's skin.

Accordingly, a need exists for a simple and inexpensive wraparound eye wear that is lightweight, collapsible and comfortable, providing a breathable enclosure to minimize perspiration and resulting wearer irritation while concurrently enhancing retention on the face of the wearer during dynamic activity.

SUMMARY OF THE INVENTION

The present invention is lightweight, collapsible and comfortable eye wear. The eye wear includes a flexible film-like lens whose natural relaxed state is a somewhat rolled-up configuration. To place the apparatus on the face of a wearer, the lens is unrolled from its natural relaxed state to wraparound the wearer's eyes from temple to temple. Once unrolled and placed in position across the wearer's eyes, a return force is created by the natural desire of the resilient film-like material to equalize forces of stress by returning to its natural unstressed relaxed state. The lens return force creates a clamping force at each edge of the lens to partially retain the lens on the face of the wearer. The eye wear assembly also includes an adjustable, elastic retention band to augment the clamping forces and snugly retain the eye wear in its proper position on the face of the wearer.

Several foam-like pads extend from the inside concave surface of the lens to rest against the wearer's face and provide a means of cushioning. These pads are distributed about the edges of the lens in a manner that creates gaps/vents which allow air to naturally circulate between the lens and the face of the wearer. The enhanced breathability minimizes perspiration, reduces lens fogging and increases overall comfort while in use. The foam pads are soft, resilient and sufficiently compressible to allow the lens to be rolled-up to fit within a small cylindrical storage container.

To use the present invention, the eye wear assembly is first removed from its small cylindrical container. The lens is then unwrapped so that it may be placed over the eyes of the intended wearer, with its pads adjacent the wearer's face. The lens is initially at least partially held in place by the clamping force generated by the stretching of the lens during unwrapping, causing the left and right wings to press against and frictionally engage the temples of the wearer. Once the lens is in place on the wearer's face, the elastic retention band may then be stretched to wrap about the rear of the wearer's head, increasing the assurance that the lens will be snugly secured.

Temple pads are attached to the rear concave surface of the wings of the lens to spread the wing clamping force across a greater area of the wearer's temples, thereby reducing the pressure on the wearer's temples and minimizing wearer discomfort. The temple pads also set the lens off from the face of the wearer to enhance air circulation between the face of the wearer and the lens.

Hence, the present invention provides wraparound eye wear which may be snugly secured on the face of the user while providing an increased level of comfort. In addition, the present invention provides a means for quickly and easily storing the entire assembly in a small container, such as a container approximately the same size as that which normally contains a roll of 35 mm film.

OBJECTS OF THE INVENTION

Accordingly, a primary object of the present invention is to provide an eye wear assembly that includes strategically placed pads to enhance comfort while being worn, yet still allows the assembly to be collapsed for storage in a small cylindrical container.

Another object of the present invention is to provide an eye wear assembly that includes a retention band to enhance retention of the assembly on the face of the wearer.

Another object of the present invention is to provide an eye wear assembly that includes strategically placed pads which set the lens of the assembly off from the face of the wearer to increase cooling air circulation and minimize lens fogging during use.

Another object of the present invention is to provide an eye wear assembly that includes strategically placed pads on the film-like lens which prevent the lens from resting directly on the skin of the wearer, thereby minimizing induced perspiration and increasing comfort for the wearer.

Another object of the present invention is to provide an eye wear assembly with a resilient lens whose relaxed state is in a closed spiral or circular configuration such that, when installed, the lens is at least partially held in place by clamping forces created when the lens is unwrapped to form an open crescent shape to extend across the eyes of the wearer from temple to temple.

Another object of the present invention is to provide an eye wear assembly with a resilient lens that does not pinch the wearer's face when installed, providing a more comfortable wearing experience.

Another object of the present invention is to provide an eye wear assembly with a resilient lens that includes offsetting and comfort enhancing resilient foam pads, along with a retention band, but can still be rolled to fit within a cylindrical container approximately the size of a typical plastic container used for storing individual rolls of 35 millimeter film.

Another object of the present invention is to provide an eye wear assembly of simple and reliable manufacture from commonly available materials.

Other further objects of the present invention will become apparent form a careful reading of the included drawing figures, the claims and detailed description of the invention.

BRIEF DESCRIPTION OF THE DRAWINGS

FIG. 1 is a perspective view showing the eye wear assembly of the present invention in place on the head of a user.

FIG. 2 is a front perspective view of the present invention when unrolled to an unnatural worn state.

FIG. 3 is a rear perspective view of the present invention when unrolled to an unnatural worn state.

FIG. 4 is a top plan view of the present invention, depicting the lens in its unnatural worn state with a phantom view of the lens moving toward its natural relaxed state superimposed therein.

FIG. 5 is a perspective view of the present invention in a rolled configuration for storage in the illustrated cylindrical container.

DESCRIPTION OF THE PREFERRED EMBODIMENTS

Figure 6:
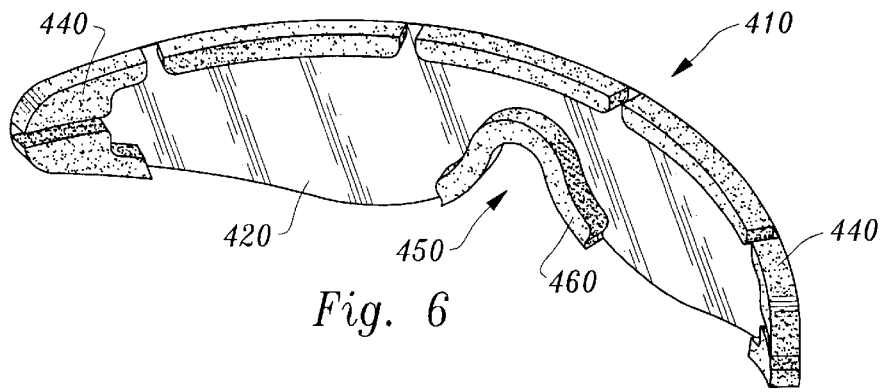
FIG. 6 is a perspective view of a lens and pad assembly of a most preferred embodiment of this invention.
Figure 7:
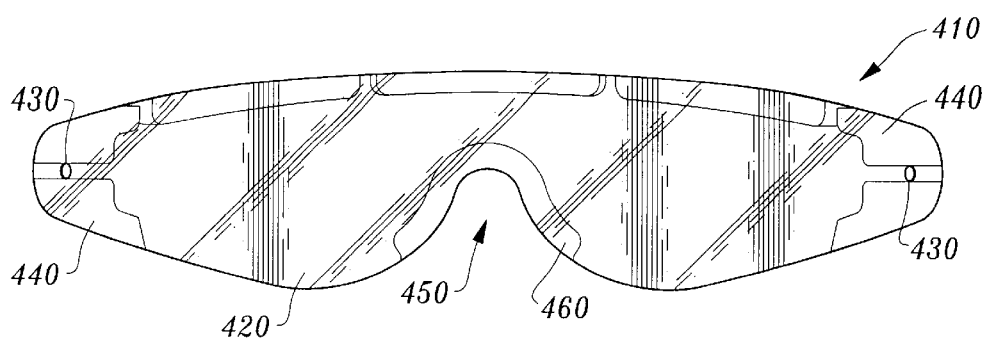
FIG. 7 is a front elevation view of that which is shown in FIG. 6.
Figure 8:
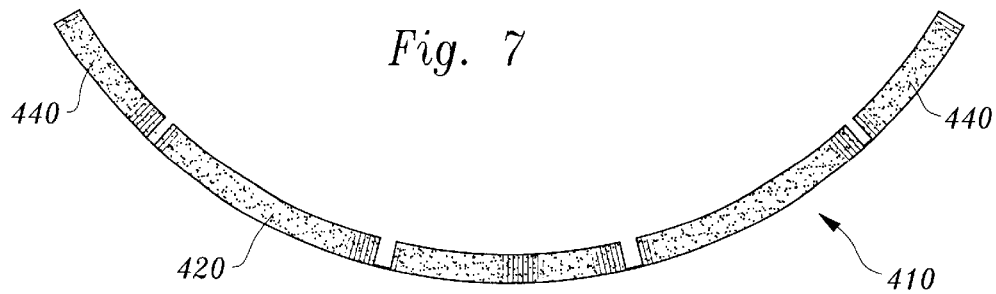
FIG. 8 is a top plan view of that which is shown in FIG. 6.
Figure 9:
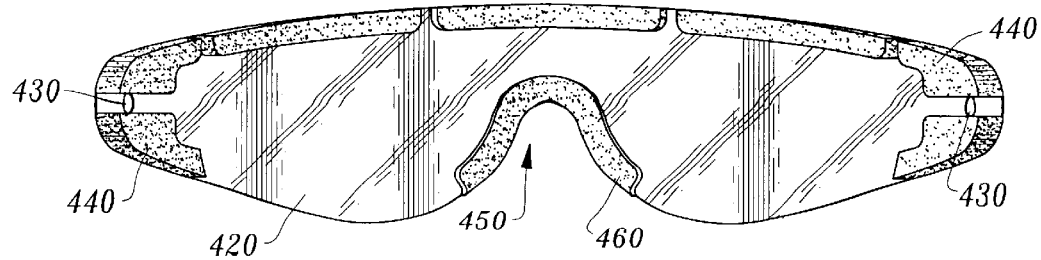
FIG. 9 is a rear elevation view of that which is shown in FIG. 6.

Referring to the drawings, wherein like reference numerals represent like parts throughout the various drawing figures, reference numeral 10 is directed to a collapsible eye wear assembly. The eye wear assembly 10 includes a resilient, flexible lens 20 which may be easily rolled up about its vertical axis to be stored in a cylindrical container 300 of the type used to store a roll of 35 millimeter camera film. The inclusion of strategically-located pads 60 and a retention band 200 increases the comfort during use of the present invention and extends the range of use of this type of lens 20 for more dynamic athletic activity.

In essence, and with particular reference to FIG. 2, the basic details of the eye wear assembly 10 are described. The assembly 10 includes a flexible resilient film-like, collapsible lens 20 that may be unrolled and extended to wrap about the eyes of the wearer W from temple T to temple T. The lens 20 is at least partially transparent. The lens 20 is partially held in place by closure forces generated within its left and right wings 30, causing respective left and right temple pads 40 to frictionally engage the wearer's W temples T. The lens 20 is offset from the wearer's W forehead by horizontal pads 60 which increase the wearer's W comfort. Two primary vents 70 provide circulation to allow perspiration to dissipate from a space between the lens 20 and the wearer's W face.

A nose cutout region 90, generally conforming to the cross-sectional shape of a typical wearer's W nose, is provided at the midpoint of the lens 20 at its bottom edge 28. A nose saddle 100, made of soft, resilient foam or rubber-type material, is attached adjacent the nose cutout region 90 on the rear concave surface 24 of the lens 20. The nose saddle 100 conforms to the shape and contour of the nose N of the wearer W. A retention band 200 extends from the left and right edges 32 of the left and right wings 30 to wrap about the rear of the wearer's W head H and provide a secure means for retaining the lens 20 on the face of a wearer W. A cylindrical container 300 is provided for stowage of the eye wear assembly 10 in a rolled-up orientation.

More specifically, and with particular reference to FIGS. 2–5, details of the lens 20 are provided. The lens includes a front convex surface 22 opposite a rear concave surface 24. The lens 20 is preferably made of a film-like resilient hydrocarbon polymeric material that can be repeatedly rolled and unrolled about its vertical axis without exceeding the elastic limit of the material from which the lens 20 is formed. The lens 20 material preferably has sufficient fatigue resistance to allow repeated cycling of the lens 20 between a stressed installed position to a tighter rolled-up storage orientation for a reasonable duration of use without tearing or cracking.

The lens 20 is at least partially transparent and may be tinted or untinted, depending on its intended use. For example, if used as post-mydriatic sunglasses, the lens 20 would be tinted to prevent discomfort caused by an ophthalmic patient's increased sensitivity to light. Alternatively, a cyclist might wish to use the eye wear assembly 10 to simply protect his or her eyes from the drying effects of the wind and the bugs or other irritating particles which are frequently encountered while cycling. In this circumstance, the lens 20 may remain untinted to maximize clarity of vision. Additionally, the lens 20 could also be made from resilient material which automatically changes the degree of tinting in proportion to the level of ambient light.

When unrolled from a relaxed state (FIG. 4, phantom view) and stretched to a slightly crescent-shaped orientation (FIGS. 2–4), the curved profile of the lens 20 is adapted to conform to the facial profile of a wearer W. In an installed position on a person's head H (FIG. 1), the rear concave surface 24 (FIG. 3) of the lens 20 is oriented closest to the person's face. The lens 20 has a generally horizontal top edge 26 (FIG. 3) which, in an installed position, is generally aligned with and adjacent to the wearer's W forehead and brow. The top edge 26 extends between left and right edges 32 of the lens 20, defining the uppermost portion of the lens 20. The lens 20 has an opposing bottom edge 28 (FIG. 3) which, in an installed position, is disposed adjacent that portion of the wearer's W face below the eyes and across the cheekbones and nose N. The bottom edge 28 extends between the left and right edges 32 of the lens 20, defining the lowermost portion of the lens 20.

As shown in FIG. 1, the lens 20 wraps around the face of the wearer W from temple T to temple T. The lens 20 includes left and right wings 30 (FIGS. 2–4) which, in an installed position, are disposed immediately adjacent the left and right temples T of the wearer W, respectively. The left and right wings 30 include corresponding left and right curved edges 32 at their furthest ends. In the prior art, these edges 32 provided the sole means for retaining the lens 20 on the face of the wearer W by pressing into the temples T slightly behind the wearer's W eyes.

In the present invention, frictional engagement at the wearer's W temples T is provided by separate left and right temple pads 40. The temple pads 40 are preferably adhesively attached to the rear concave surface 24 of the lens 20 adjacent the left and right edges 32 of the left and right wings 30. The temple pads 40 are somewhat crescent-shaped and preferably made of soft foam rubber-like resilient material that cushions and spreads the clamping force (as shown by Arrow A in FIG. 4) to minimize any discomfort to the wearer W which would normally be caused by the impingement of the sharp edges 32 of the wings 30 upon the skin of the temples T of the wearer W. The temple pads 40 are shaped to conform to the curved profile of the edges 32 of the wings 30. The temple pads 40 have upper ends 42 which are disposed closest to, but preferably not past, the top edge 26 of the lens 20. Lower ends 43 are disposed closest to, but preferably not past, the bottom edge 28 of the lens 20. The temple pads 40 each extend from a forward portion 44 to a rear portion 45. The rear portion 45 conforms to the shape of the edge 32 of the wing 30, extending from the lower end 43 to the upper end 42 of the temple pad 40.

The temple pads 40 include gripping faces 46 (FIG. 3) furthest away from the rear concave surface 24 of the lens 20. The gripping faces 46 rest against and frictionally engage the wearer's W temples T when the lens 20 is installed. The temple pads 40 also include a lens face 47 which provides a surface to adhesively secure the temple pad 40 to the rear concave surface 24 of the lens 20. The temple pads 40 have sufficient thickness and resiliency to maintain a slight separation between the rear concave surface 24 of the lens 20 and the wearer's W face.

The temple pads 40 serve multiple purposes including the following. First, the gripping faces 46 of the temple pads 40 increases the area of the wearer's W temple T to which the clamping force A (FIG. 4) is applied, thereby decreasing the pressure directly applied at any point to the wearer's W temples T and eliminating the irritating uncomfortable pinching encountered in the prior art. Second, the gripping faces 46 preferably have minimally roughened surfaces which increase the frictional engagement between the temple pad 40 and the wearer's W temples T, enhancing lens 20 retention. In the prior art, the lens 20 would tend to slip off the wearer's W temples T if the clamping force A was insufficient, particularly where the static friction between the edges 32 of the lens 20 and the wearer's W temples T was reduced by the lubricating effect of the wearer's W own perspiration on the plastic film-like surface of the lens 20. Third, the temple pads 40 set the wings 30 of the lens 20 off slightly from the skin of the wearer's W temples T. This allows the wearer's W skin to breathe and remain cool, thereby minimizing induced perspiration which would reduce the static friction between the gripping face 46 of the temple pads 40 and the skin of the wearer's W temple T. Fourth, the temple pads 40 provide a means to absorb induced perspiration, thereby minimizing the lubricating effect. Fifth, as perspiration is absorbed by the temple pad 40, it subsequently evaporates to create a cooling wicking effect, lowering the temperature of the pad 40, and reducing the tendency for further induced perspiration.

Elongate left and right horizontal pads 60, along with an elongate center pad 62, are adhesively secured along the top edge 26 of the lens 20. The pads 60, 62 are preferably rectangular box-like in shape and made from soft resilient foam-like material. Each pad 60, 62 has a rectangular top side 64 which is preferably aligned with, but does not extend beyond, the top edge 26 of the lens 20. The top side 64 extends perpendicularly from the rear concave surface 24 of the lens 20. The pads 60, 62 also include an opposing bottom side 65 which extends perpendicularly from the rear concave surface 24 of the lens 20 in a plane preferably parallel to the top side 64. The pads 60, 62 have an anterior face 66 (FIG. 2) which provides a surface to adhesively attach the pads 60, 62 to the rear concave surface 24 of the lens 20 along the top edge 26. The pads 60, 62 also include an opposing parallel posterior face which lies immediately adjacent the brow and forehead of the wearer W when the eye wear 10 is in use. The horizontal pads 60 and the center pad 62 serve functions similar to the temple pads 40 discussed above, including creating an offset of the lens from the wearer's W face, absorbing perspiration, increasing static friction to enhance retention, and increasing circulation about the lens and the wearer's W face to create a cooling effect.

The pads 60, 62 are preferably distributed immediately along the top edge 26 of the lens 20 in a manner that creates at least two separate vents 70. The left horizontal pad 60 is disposed closest the left wing 30; the right horizontal pad 60 is disposed closest the right wing 30; the center pad 62 is disposed between, but not touching, the left and right horizontal pads 60.

The vents 70 provide an additional means to allow air to easily circulate between the rear concave surface 24 of the lens 20 and the face of the wearer W. The vents 70 allow moisture vapor created by the perspiration of the wearer W to escape from the space between the lens 20 and the face of the wearer W during use. The size of the vents 70 may be adjusted to increase air circulation by either shortening the pads 60, 62 or increasing the amount of separation between the pads 60, 62. The vents 70 are provided along the top edge 26 of the lens 20 to allow warmer, moist air behind the lens to escape in a vertical direction as a result of the natural convection tendency for warmer air to rise due to its decreased density. The air within the enclosure is heated by light impinging on the lens and/or body heat radiating from the wearer's W face. Although only three pads 60, 62 and two vents 70 are shown in the drawings, the size of each pad 60, 62 could be decreased while the number of pads 60, 62 could be increased, thereby increasing the number of vents 70 to potentially further enhance circulation.

The vents 70 also allow the lens 20 to be more easily rolled-up by providing gaps between the pads 60, 62. Unlike the lens 20, whose natural tendency is to close in a spiral, the pads 60, 62 could typically be biased toward a flat, planar state. Hence, when the pads 60, 62 are attached to the rear concave surface 24 of the lens 20, the pads 60, 62 tend to cause the lens 20 to unspiral. If the pads 60, 62 were continuous with no vents 70, as the lens 20 was rolled into a spiral, the pads 60, 62 would generate an opposing unwrapping force that would make it much more difficult for the user to roll-up the lens 20 to fit within the cylindrical container 300. As the thickness of the pads 60, 62 increase, the unwrapping force would also increase proportionally. Hence, one would likely have to minimize the thickness of the pads 60, 62 to facilitate ability to roll-up the lens 20 to fit within the container 300.

In addition, if continuous without any vents 70, the pads 60, 62 would tend to crease at various points along their posterior face 67 as the lens 20 was rolled-up. The vents 70 provide discontinuities in the pads 60, 62 that provide sufficient space to act as a means of stress relief, thereby reducing the tendency for the pads 60, 62 to crease. Additionally, the vents 70 provide actual physical space to allow the lens 20 to be rolled-up without causing adjacent pads 60, 62 to fold in on each other, thereby reducing the unwrapping force and easing one's ability to roll-up the lens 20 to fit within the cylindrical container 300.

Consequently, inclusion of the vents 70 allows the thickness of the pads 60, 62 to be increased sufficiently to provide adequate cushioning on the wearer's W face. In addition, increased pad 60, 62 thickness increases offset of the lens 20 from the wearer's W face, thereby increasing cross-sectional area of the vents to enhance air circulation about the lens 20.

A nose cut-out region 90 is located in the lower portion of the lens 20 at the approximate mid-point of the bottom edge 28. The nose cut-out region 90 is shaped to receive and generally conform to the typical wearer's W cross-sectional nose N profile. The nose cut-out region 90 has a crest 92 formed at the convergence of a left and right side 94. The crest 92 corresponds to the ridge R of the wearer's W nose N. The sides 94 correspond to the contour of the wearer's W nose N along its sides adjacent the nostrils.

With particular reference to FIG. 3, the details of a nose saddle 100 of the present invention are described. The separate nose saddle 100 is preferably adhesively attached along a mounting face 150 to the rear concave surface 24 of the lens 20 to follow the contour along the edges of the nose cut-out region 90. The nose saddle 100 may be attached to the lens 20 by other means. Velcro strips may be adhesively attached to the rear concave surface 24 of the lens 20 along the sides 94 of the nose cut-out region 90 which correspond to mating velcro strips adhesively attached to the mounting face 150 of the nose saddle 100. This means of attachment would allow the nose saddle 100 to be changed to accommodate varying nose N profiles of different wearers W.

Additionally, the nose saddle 100 may include a resilient groove molded within the upper surface 140 and mounting face 150 of the nose saddle 100. The resilient groove would have a gap thickness that is slightly less than the lens 20 thickness along the nose cut-out region 90. The nose saddle 100 could then frictionally engage the front convex surface 22 and the rear concave surface 24 of the lens 20. This means of attachment would also allow the nose saddle 100 to be changed to accommodate varying nose N profiles of different wearers W.

Similarly, the nose saddle 100 could be mounted on a separate collapsible frame which includes protrusions which can be pressed into corresponding holes distributed along the crest 92 and sides 94 of the nose cut-out region 90 of the lens 20. Again, the means of attachment would allow the wearer W to easily change the nose saddle 100.

The nose saddle 100 is preferably made of the same soft resilient, foam rubber material as the pads 40, 60, 62. The saddle 100 includes an apex 110 which corresponds to the crest 92 of the nose cut-out region 90. A left and right leg 120 of the saddle 100 corresponds to the left and right sides 94 of the nose cut-out region 90. The legs 120 have tips 122 at their lowest end closest to the bottom edge 28 of the lens 20. The saddle 100 extends away from the rear concave surface 24 of the lens 20 to form a lower surface 130 which, in an installed position, is located against the skin of the nose N of the wearer W. The nose saddle 100 also includes the mounting face 150 which provides a surface to adhesively attach the saddle 100 to the rear concave surface 24 of the lens 20. The mounting face 150 of the saddle 100 extends sufficiently beyond the bottom edge 28 of the lens 20 along the nose cut-out region 90 to ensure that the bottom edge 28 of the lens 20 does not come into contact with the wearer's W nose N.

As with the temple pads 40, the saddle 100 provides another means to improve retention of the lens 20 on the wearer's W face while simultaneously increasing the wearer's W comfort. In the prior art, the bottom edge 28 of the nose cut-out region 90 tended to slip down and uncomfortably impinge along the bottom edge 28 of the lens 20 on the wearer's W nose N. By incorporating the nose saddle 100 of the present invention, the bottom edge 28 of the lens 20 is prevented from pressing into the wearer's W nose N or upper cheek bone area. Any downward force caused by the weight of the lens 20 is cushioned by the nose saddle 100 and spread across the area of the lower surface 130 of the nose saddle 100. As with the other pads 40, 60, 62, the nose saddle 100 increases air circulation, absorbs perspiration, and has inherent wicking effect, all of which increase the wearer's W comfort during use.

With particular reference to FIG. 1, the details of a retention band 200 of the present invention are described. The flexible retention band 200 is interposed between the wings 30 of the lens 20 to provide an additional means to snugly secure the lens 20 on the wearer's W face. The band 200 includes separate left and right elongate tubular connectors 210 which extend rearward from the edges 32 of the wings 30. The connectors 210 are attached to the lens 20 at their fixed ends 212 and extend to terminate at movable distal ends 214. The connectors 210 are preferably made from a resilient hydrocarbon polymeric material with sufficient rigidity to cause the connectors 210 to extend laterally rearward from the wing 30 of the lens 20, yet sufficiently flexible to allow the connectors 210 to bend in a manner comporting with the collapsed, rolled-up orientation of the lens 20, thereby allowing the entire eye wear assembly 10 to be stored in the small portable cylindrical container 300.

An elongate elastic strap 220 is connected to the distal ends 214 of the connectors 210. The elastic strap 220 preferably has a length that is less than that necessary to travel around the wearer's W head H when not stretched, but sufficient to allow the strap 220 to be stretched sufficiently to be passed around the wearer's W head H without exceeding the elastic limit of the strap 220. An adjusting clip 230 encloses the elastic strap 220 at its midpoint to provide a means for further shortening the elastic strap 220 to increase the tension within the strap 220 ensuring a snug fit on the face of the wearer W.

With particular reference to FIG. 5, the details of the cylindrical storage container 300 to be used for housing the eye wear assembly 10 in a rolled-up orientation are described. The eye wear assembly 10 and lens 20 are designed to allow storage within the small cylindrical container 300. The container 300 is preferably made from a lightweight, inexpensive hydrocarbon polymer material. The cylindrical container 300 includes a circular floor 302 from which extends a cylindrical side wall 304, to form the can or receiver portion of the container 300. At an open end 303, the container 300 includes a rim 306 circumferentially disposed along the upper edge of the side wall 304 to provide a means for securing a cap 310 to the top of the container 300.

In use and operation, the eye wear assembly 10 is first removed from the cylindrical storage container 300. The lens 20 will naturally unroll from its compressed storage state (FIG. 5) to its natural relaxed state (approximated by FIG. 4, phantom view in broken lines). The wearer W then grasps the lens 20 at each wing 30 and further unrolls the lens 20 from the relaxed state until the wings 30 are sufficiently spread to allow the lens 20 to be placed on the wearer's W face, with the nose saddle 100 seated upon the bridge of the wearer's W nose N and the temple pads 40 resting against the wearer's W temples T (FIG. 1).

As the lens 20 is set in place on the wearer's W face, the elastic strap 220 of the retention band 200 is simultaneously stretched and positioned over the back of the wearer's W head H to seat the lens comfortably on the wearer's W face and provide an added level of retention. The retention band 200 can be tightened, if desired by the wearer W, by pulling the elastic strap 220 through the adjusting clip 230, thereby shortening the strap 220. The eye wear assembly 10 is then positioned on the wearer's W face in the manner shown in FIG. 1.

The eye wear 10 is removed by simply reversing the above procedure. The lens 20 will then return to its relaxed state (FIG. 4, phantom view), from which the lens 20 is rolled-up with the retention band 200 (FIG. 5) and inserted into the container 300.

Figure 10:
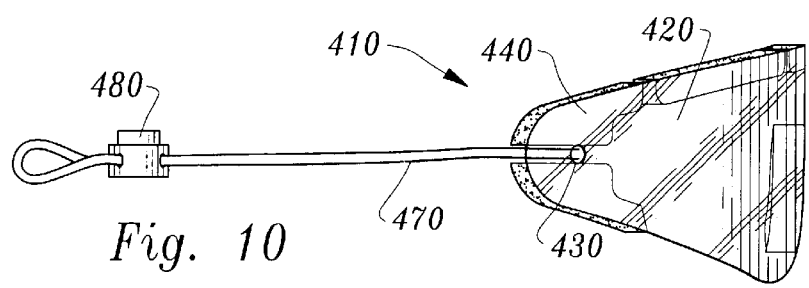
FIG. 10 is a side elevation view of that which is shown in FIG. 6.
Figure 11:
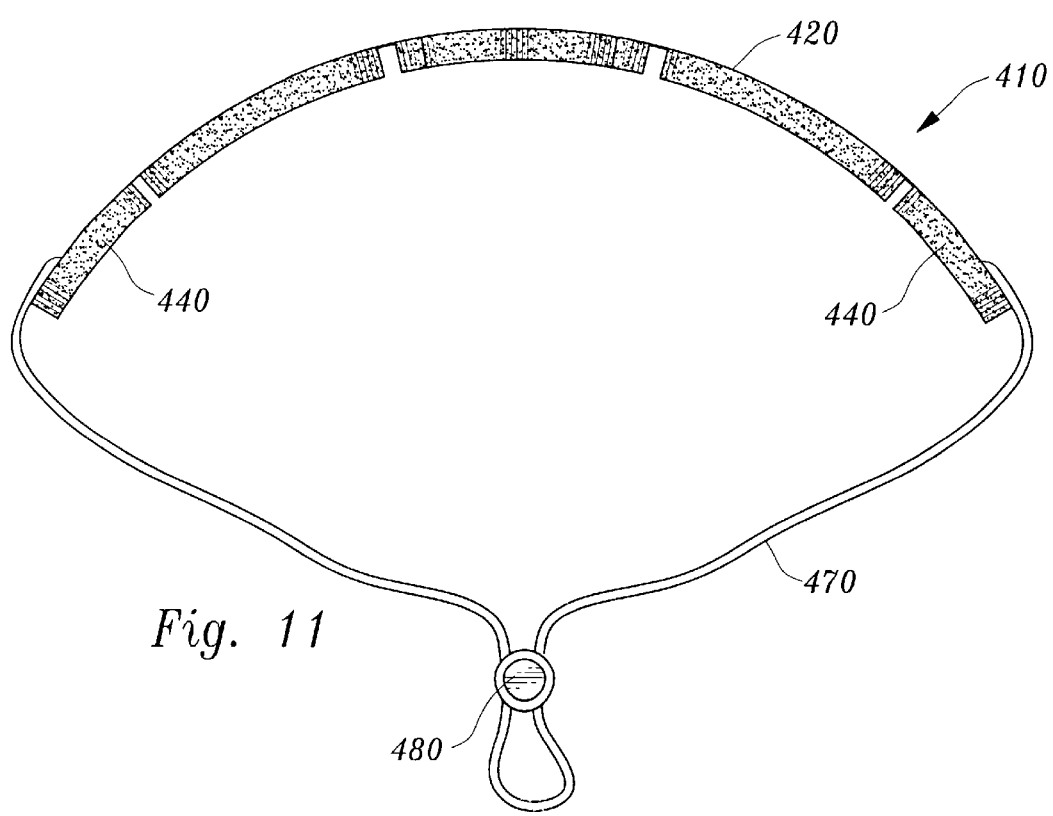
FIG. 11 is a bottom plan view of that which is shown in FIG. 6 and with a cord of this embodiment attached thereto.
Figure 12:
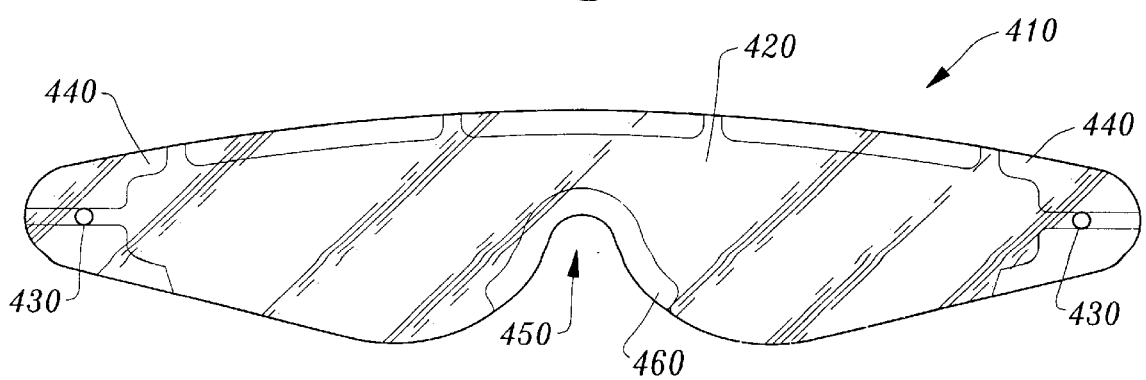
FIG. 12 is a front elevation view of that which is shown in FIG. 6 but with the lens rolled out flat.
Figure 13:
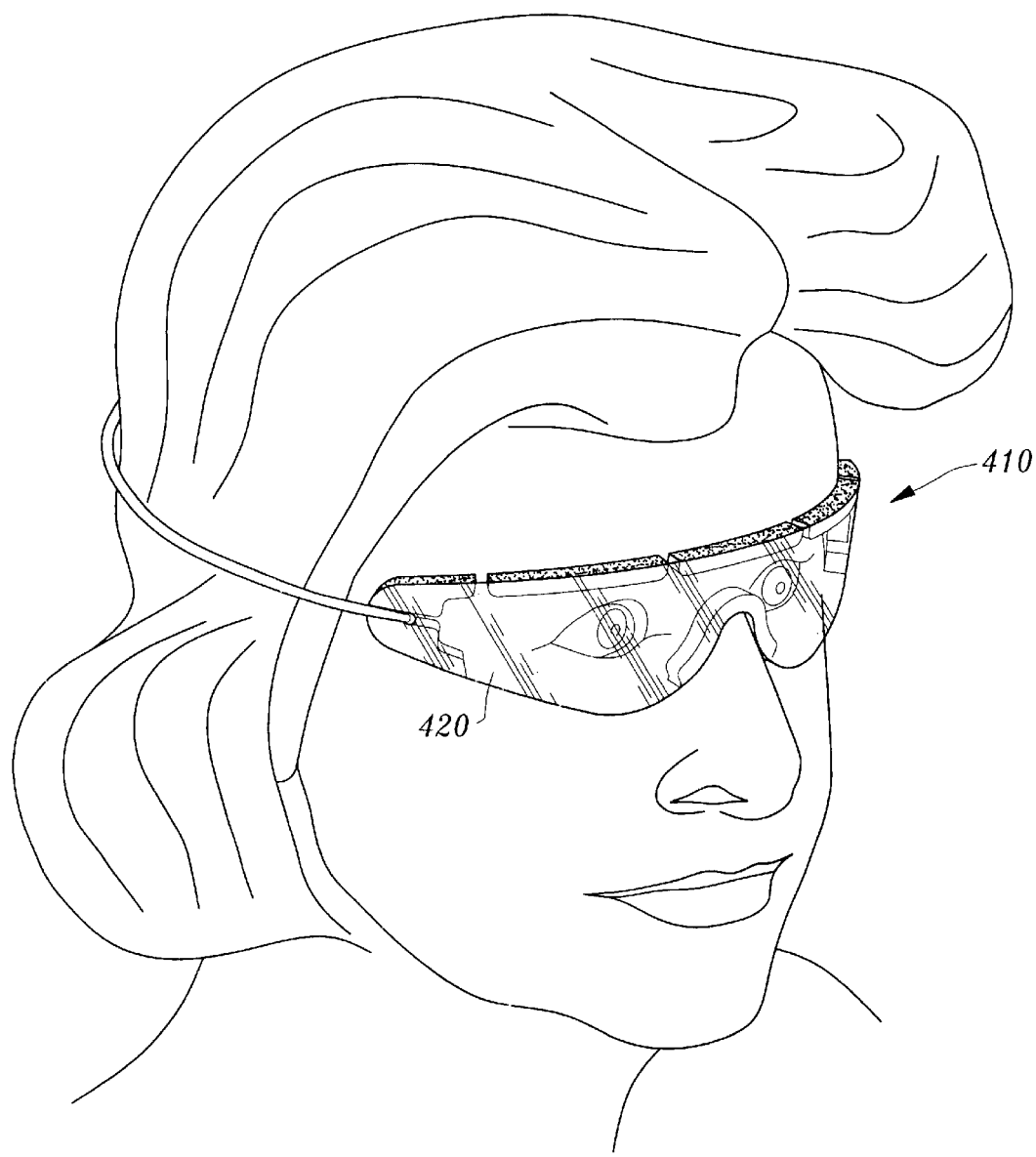
FIG. 13 is a perspective view of that which is shown in FIG. 6 along with a cord and in position on a head of a user.

FIGS. 6–13 show details of a most preferred eye wear assembly 410. This most preferred eye wear assembly 410 is similar to the assembly 10 described in detail above except where specifically identified below. Hence, the preferred eye wear assembly 410 includes a single lens 420 shaped to cover both eyes of a wearer. Holes 430 are provided adjacent each side edge of the lens 420. These holes 430 are sized at least as large as a diameter of a cord 470 (FIGS. 10, 11 and 13). Hence, the cord 470 can pass through the hole 430. Side pads 440 are located adjacent the side edges of the lens 420. The side pads 440 are on an inside surface of the lens 420 and preferably substantially entirely cover the inside surface of the lens 420 adjacent the side edges of the lens 420. The side pads 440 thus extend further in height from top and bottom edges of the lens 420 than do other pads such as the bridge pad 460 (FIGS. 6, 7, 9 and 12) and three or more brow pads extending along a top edge of the inside surface of the lens 420.

Each side pad 440 preferably includes a recess 442 adjacent the hole 430. This recess 442 is larger than the hole 430 so that the cord can pass both through the hole 430 and the recess 442. Because the recess 42 is larger than the hole 430, a knot or other appendage on the cord 470 which is larger than a diameter of the cord 470 can reside within the recess 442. This cord appendage thus keeps the end of the cord 470 from passing through the hole 430 sufficiently to take the cord 470 out of the hole 430. The recess 442 also provides a location for the cord appendage so that when the preferred eye wear assembly 410 is worn, the cord appendage does not impact the wearer's temple. Rather, the side pads 440 surrounding the recess 442 impact the wearer's temple and the cord appendage or knot remains within the recess 442.

The assembly 410 additionally includes a nose cut-out 450 similar to that of the assembly 10 described in detail above. A bridge pad 460 is located adjacent the nose cut-out 450. The bridge pad 460 of this preferred eye wear assembly 410 has a height above a bottom edge of the lens 420 similar to a height of other pads adjacent the top edge of the lens and is formed from a similar material as all the other pads, such as the side pads 440.

The cord 470 preferably is an elastic cord with ends adjacent the holes 430 and a midpoint of the cord 470 including an adjusting clip 480 thereon. As an alternative, the cord 470 can have one or both ends attached to the lens or pads through fasteners, adhesive or other connectors than the hole 430. The adjusting clip 480 allows an effective length of the cord 470 between ends of the cord 470 to be increased or decreased. The adjusting clip 480 can be in the form of a spring biased clamp which can pinch portions of the cord 470 passing through the adjusting clip 480 when left in a resting position, but which releases the cord when a button on the adjusting clip 480 is depressed, so that the cord can be fed into and out of the adjusting clip 480 freely when this button is depressed. Other forms of adjusting clips 480 could similarly be used which rely on friction or other cord engagement structures.

The preferred eye wear assembly 410, like the assembly 10 described above, does not require that the lens 420 be sufficiently biased towards a rolled-up position that it can hold itself over the wearer's eyes merely with clamping force of the lens 420 attempting to return to its rolled-up configuration. Rather, the eye wear assemblies 10, 410 can be unbiased or only slightly biased towards a rolled-up or non-rolled-up configuration. With such an arrangement the function of the cord 470 is enhanced. Specifically, the cord 470 is preferably elastic and provides sufficient rearward forces on the lens 420 of the eye wear assembly 410 to cause the eye wear assembly 410 to engage the face of the wearer over the eyes of the wearer. This tension can be increased or decreased by adjusting a position of the adjusting clip 480 upon the cord 470. The eye wear assembly 410 is still sufficiently flexible that it can be rolled-up into a cylinder for containment within a small cylindrical container (FIG. 5).

This disclosure is provided to reveal a preferred embodiment of the invention and a best mode for practicing the invention. Having thus described the invention in this way, it should be apparent that various different modifications can be made to the preferred embodiment without departing from the scope and fair meaning of this disclosure.

What is claimed is:

1. An apparatus for protection of eyes of a human wearer, comprising in combination:

a lens including a left edge defining a left side of said lens and a right edge defining a right side of said lens;

said lens having sufficient width between said left edge and said right edge to cover both eyes of the wearer;

said lens formed of at least partially transparent material;

said lens being sufficiently flexible about a vertical axis to be orientable in both a plane and in a rolled-up orientation exhibiting at least partial overlap, without exceeding an elastic limit of said material forming said lens; and at least one pad adjacent said left edge of said lens and at least one pad adjacent said right edge of said lens, said left pad and said right pad in positions where said pads abut temples of the wearer when said lens is worn.

2. The apparatus of claim 1 wherein said pad adjacent said left edge is spaced from said pad adjacent said right edge by at least one gap.

3. The apparatus of claim 2 said apparatus includes at least three pads including said pad adjacent said left edge, said pad adjacent said right edge and a center pad between said pad adjacent said left edge and said pad adjacent said right edge, each said pad spaced from adjacent said pads by at least one gap, such that said center pad does not touch said pad adjacent said left edge and said center pad does not touch said pad adjacent said right edge.

4. The apparatus of claim 3 wherein said lens includes at least five pads thereon, each said pad spaced from adjacent said pads by a gap, such that none of said at least five pads touch each other, said gaps extending substantially vertically between adjacent said pads.

5. The apparatus of claim 4 wherein said pads each have a uniform thickness extending away from said lens and each of said at least five pads are located adjacent a top edge of said lens.

6. The apparatus of claim 5 wherein each of said at least five pads has a uniform height extending down from said top edge of said lens for at least a portion of each of said pads.

7. The apparatus of claim 1 wherein each said pad is formed from a common material having a similar flexibility, and wherein said lens includes a nose cutout and a saddle adjacent said bottom edge of said lens at said nose cutout, said saddle formed from a material similar to a material forming said pads.

8. The apparatus of claim 7 wherein said saddle has a thickness and a height above said bottom edge similar to a thickness and a height below said top edge of pads of said apparatus located adjacent said top edge.

9. The apparatus of claim 1 wherein said at least one pad adjacent said left edge and said at least one pad adjacent said right edge extend further from edges of said lens than at least one pad that is spaced from said left edge and said right edge of said lens and adjacent said top edge of said lens.

10. The apparatus of claim 1 wherein said pad adjacent said left edge and said pad adjacent said right edge include a recess therein, said lens including at least one hole passing therethrough at said recess in said pad, said recess being larger than said hole, such that a cord can pass through said hole and through said recess in each said pad adjacent said left edge and said right edge.

11. The apparatus of claim 10 wherein said cord is elastic and includes a cord appendage at each end of said cord, said cord appendage having a size larger than said hole in said lens and smaller than said recess, such that said appendage can abut against said lens within said recess in said pad adjacent said left edge and said pad adjacent said right edge, with said appendage keeping said cord from coming out of said hole.

12. The apparatus of claim 11 wherein said cord is length adjustable at an adjusting clip between ends of said cord.

13. A method for storing eyeglasses when not in use, the eyeglasses having a lens including a left edge defining a left side of the lens and a right edge defining a right side of the lens, the lens having sufficient width between the left edge and the right edge to cover both eyes of the wearer, the lens formed of at least partially transparent material, the lens being sufficiently flexible about a vertical axis to be orientable in both a plane and in a rolled-up orientation exhibiting at least partial overlap, without exceeding an elastic limit of the material forming the lens, at least one pad adjacent the left edge and at least one pad adjacent the right edge; the steps including:

rolling the lens up into a spiral orientation with the edges overlapping;

providing a cylindrical container having a diameter similar to a diameter of the lens when the lens is in its rolled-up orientation, the container diameter sized smaller than both a horizontal length and a vertical height of the lens when the lens is deployed for wearing; and placing the lens into the container.

14. The method of claim 13 wherein the cylindrical container includes a cap, the cap including means to attach to the cylindrical container.

15. The method of claim 13 wherein the lens is rolled-up into a tighter spiral than is achieved by the relaxed orientation for the lens such that the lens curves at least 720° between the left edge and the right edge of the lens.

16. The method of claim 13 including the further steps of configuring the lens to include horizontal pads adjacent a top edge extending between the left edge and the right edge with vents defining gaps between portions of the horizontal pads, the vents allowing the lens to be more tightly rolled-up than would be possible without the vents.

17. An apparatus for protection of eyes of a human wearer, comprising in combination:

a lens including a left edge defining a left side of said lens and a right edge defining a right side of said lens;

said lens having sufficient width between said left edge and said right edge to cover both eyes of the wearer;

said lens formed of at least partially transparent material;

said lens being sufficiently flexible about a vertical axis to be orientable in both a plane and in a rolled-up orientation exhibiting at least partial overlap, without exceeding an elastic limit of said material forming said lens;

at least one pad adjacent said left edge of said lens and at least one pad adjacent said right edge of said lens, said left pad and said right pad in positions where said pads abut temples of the wearer when said lens is worn; and said lens including at least one hole adjacent at least one of said pads.

18. The apparatus of claim 17 wherein at least one of said pads includes a recess therein, said recess adjacent said hole.

19. The apparatus of claim 18 wherein said recess in said pad is larger than a size of said hole; and a card passing through said hole, said card having an appendage thereon which is larger than said hole and smaller than said recess.

20. The apparatus of claim 19 wherein said appendage is a knot in said cord.

* * * * *